US00PP10699P

United States Patent [19]

McGredy

[11] Patent Number: Plant 10,699

[45] Date of Patent: Nov. 24, 1998

[54] FLORIBUNDA ROSE PLANT NAMED 'MACFIRINLIN'

[75] Inventor: Sam McGredy, Auckland, New Zealand

[73] Assignee: DeVor Nurseries, Inc., Watsonville, Calif.

[21] Appl. No.: 742,144

[22] Filed: Oct. 31, 1996

[51] Int. Cl.[6] ..... A01H 5/00

[52] U.S. Cl. ..... Plt./22

[58] Field of Search ..... Plt./22, 28, 11

[56] References Cited

PUBLICATIONS

UPOVROM, Plant Variety Database, 1997 Mar., GTI Jouve Retrieval Software, Listing for 'Macfirinlin'.

*Primary Examiner*—Howard J. Locker
*Attorney, Agent, or Firm*—Christie, Parker & Hale, LLP

[57] ABSTRACT

A floribunda rose variety producing red and white bi-color flowers.

1 Drawing Sheet

BACKGROUND OF THE INVENTION

The present invention relates to a new and distinct floribunda rose variety which was originated by my crossing as seed parent the variety known as 'Howard Morrison' and as pollen parent the variety known as 'Sue Lawley'. The varietal denomination of this new rose is 'Macfirinlin'.

SUMMARY OF THE INVENTION

Among the novel characteristics possessed by this new variety which distinguish it from its parents and all other varieties of which I am aware are its attractive unusual red and white bi-color flowers borne in clusters on a bushy plant.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

Comparison with Parents

'Howard Morrison' is a small flowered crimson hybrid tea and the new variety 'Macfirinlin' produces red and white bi-color flowers. The plant of 'Sue Lawley' tend to be one-sided and ungainly as compared to 'Macfirinlin'.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.
*Seed parent.*—'Howard Morrison'.
*Pollen parent.*—'Sue Lawley'.
Class: Floribunda.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Flower

Blooming habit: Continuous.

A. Bud:
(1) *Size.*—Small.
(2) *Form.*—Urnshaped, about 2 to 2.5 cm long and about 1 to 2 cm wide.
(3) *Color.*—When sepals first divide, bud color is near 60A.
(4) *Sepals.*—Longer than bud, sepals divide and spread when bloom opens and reflex at maturity. Some leaf-shaped tips, some with leaf-like protrusions about 2 to 2.5 cm from sides. Color: Most are near 144A with near 144B toward base on top side with slightly lighter color under side.
(5) *Peduncle.*—Length: About 5.5 cm to about 7 cm. Aspect: Hairy, with small prickles. Strength: Slender but sturdy. Color: Near 144B with near 181A blush.
(6) *Bracts.*—About 2 to 3, near 146C, broadly lanceolate with caudate apex; about 4.5 to 5 cm below calyx.

B. Bloom:
(1) *Size.*—Average size when fully expanded — about 6 cm to about 7 cm.
(2) *Borne.*—Clusters of 5 to 6 blooms.
(3) *Form.*'Informal — Single.
(4) *Petalage.*—Number of petals under normal conditions — about 9 to 10.
(5) *Color* (⅓–½ *open*).— Outer petals — Top surface: Near 46A. Undersurface: Edge & Center: Near 55B with near 55D nearing base. Inner petals — Top surface: Near 46A. Undersurface: Edge & Center: Near 55B with near 55D nearing base. Base of petals: Near 4D extending upward about ¼ petal giving appearance of a creme "eye". General tonality from a distance: Red-white bi-color with occasional creme colored streaks on some petals.
(6) *Color* (*Fully open*).—Outer petals — Top surface: Near 46A. Undersurface: Top & Center: Near 55B with near 55D toward base. Inner petals — Top surface: Near 46A. Undersurface: Top & Center: Near 55B with near 55D toward base. Base of petals: Near 4D. General tonality from a distance: Red-white bi-color.

(7) *Color change.*—Color does not change.

C. Petals:

(1) *Texture.*—Thick, smooth.

(2) *Appearance.*—Inside velvety and outside somewhat matte.

(3) *Form.*—Wedge-shaped with pointed apex.

(4) *Arrangement.*—Single.

(5) *Petaloids in center.*—Few, about 1 or 2.

(6) *Fragrance.*—Slightly fruity.

(7) *Lasting quality.*—On plant about 6 to 8 days, about 4 to 6 days after cutting.

(8) *Persistence.*—Petals drop off cleanly.

Reproductive Organs

A. Stamens:

(1) *Arrangement.*—Regularly arranged around styles.

(2) *Anthers.*—Color near 149B.

(3) *Filaments.*—Color — near 167D.

(4) *Pollen.*—Color — near 167D.

B. Pistils:

(1) *Styles.*—Bunched.

(2) *Stigmas.*—Color near 14B.

C. Characteristics of hips: Globose, base elongated on one side; about 1.25 cm wide by about 1.3 cm long, near 144A with near 31A at top.

Plant

A. Form: Upright.

B. Growth: About 47 cm to about 62 cm in height at first season.

C. Foliage: Compound 3 to 5 leaflets.

(1) *Size.*—Medium about 7 to 11 cm long, about 5 to 6 cm wide.

(2) *Quantity.*—Abundant.

(3) *Color.*—New foliage — upper side near 137A underside near 147A; mature foliage — upper side near 147A, underside near 147B.

(4) *Shape.*—Oval.

(5) *Texture.*—Upper side semi-glossy, leathery; underside leathery, veiny.

(6) *Edge.*—Serrate.

(7) *Serration.*—Denticulate.

(8) *Leaf stem.*—Color — medium green.

(9) *Stipules.*—Parallel, narrow, slightly bearded.

(10) *Rachis.*—Small prickles on underside.

(11) *Petioles.*—Top near 146C, underside near 146D.

(12) *Auricle.*—Narrow, slightly bearded.

(13) *Resistance to disease.*—Moderate resistance to blackspot; very resistant to mildew and rust.

D. Wood:

(1) *New wood.*—Color — near 181A with tinges of near 144C on bark.

(2) *Old wood.*—Color — near 146B, bark smooth.

E. Flower Stem: About 21 cm to about 41 cm from last cut.

F. Thorns:

(1) *Thorns.*—Quantity: On main stalk, ordinary; laterals from stalk, ordinary. Form: Curved downward; slight wing-shaped base. Length: About 0.07 to 0.09 cm long; Color: Near 181A. Position: Irregular.

(2) *Prickles.*—Ordinary.

G. Winter hardiness: Winter hardy in Watsonville, Calif.

I claim:

1. A new and distinct variety of floribunda rose plant, substantially as shown and described.

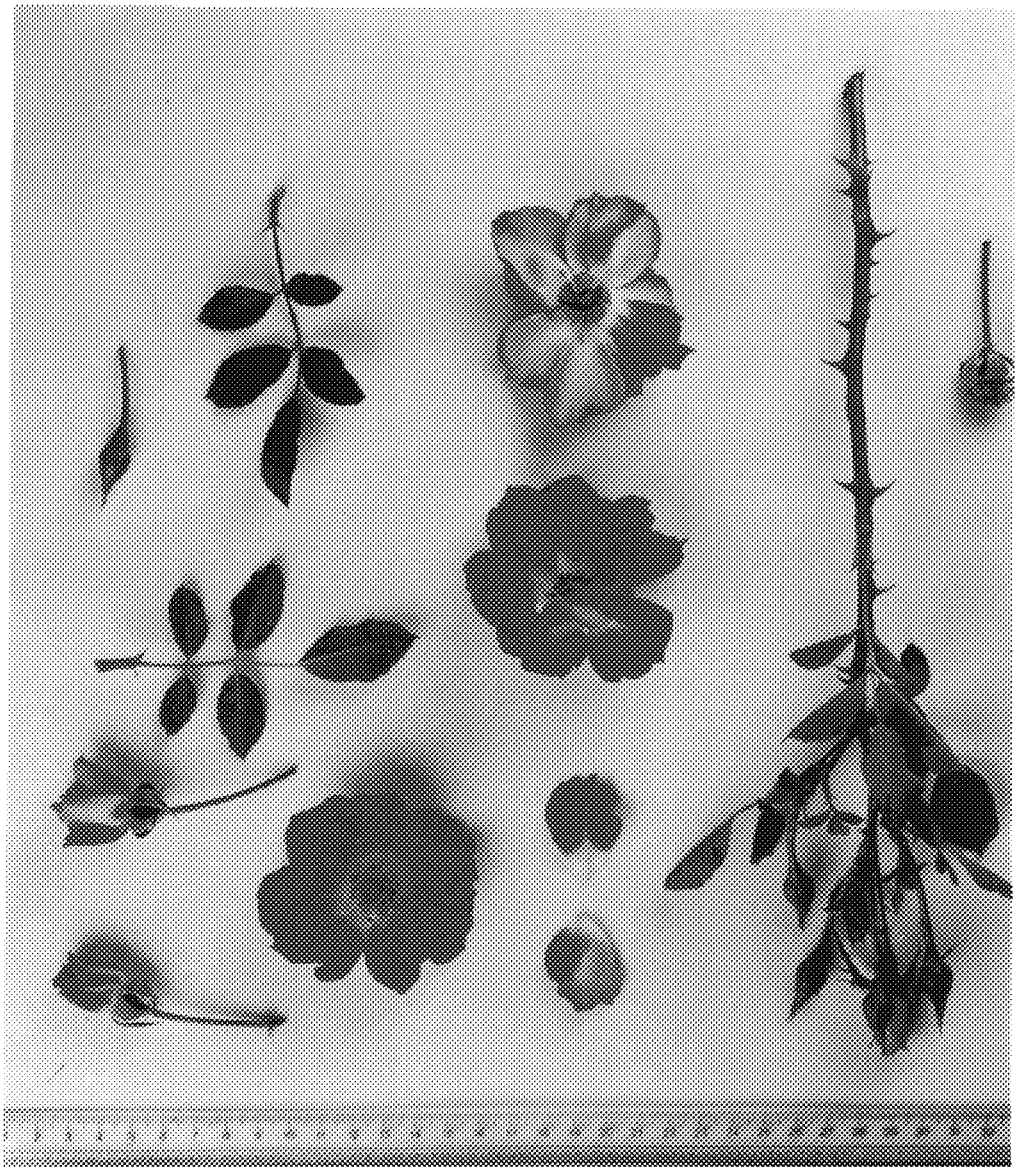

* * * * *